United States Patent

Oballa et al.

[11] Patent Number: 6,111,156
[45] Date of Patent: Aug. 29, 2000

[54] INTEGRATED HIGH TEMPERATURE HIGH CONVERSION OLEFIN/POLYOLEFIN PROCESS

[75] Inventors: Michael C. Oballa, Cochrane; David Purvis, Georgetown; Andrzej Z. Krzywicki, Calgary; Leslie W. Benum, Red Deer, all of Canada

[73] Assignee: Nova Chemicals (International) S.A., Villars-sur-Glane, Switzerland

[21] Appl. No.: 09/189,855

[22] Filed: Nov. 10, 1998

[51] Int. Cl.$^7$ ................................. C07C 2/06
[52] U.S. Cl. ................ 585/330; 585/329; 585/326; 585/512; 585/650
[58] Field of Search .................. 585/330, 329, 585/326, 512, 648, 650

[56] References Cited

U.S. PATENT DOCUMENTS

| | | | |
|---|---|---|---|
| 4,762,958 | 8/1988 | Mertens et al. | 585/650 |
| 4,780,196 | 10/1988 | Alagy et al. | 585/650 |
| 4,935,569 | 6/1990 | Harkins et al. | 585/328 |
| 5,162,595 | 11/1992 | Wu | 585/512 |
| 5,321,107 | 6/1994 | Tsutsui et al. | 585/512 |
| 5,430,211 | 7/1995 | Pogue et al. | 585/323 |
| 5,463,154 | 10/1995 | Slim et al. | 585/261 |
| 5,488,148 | 1/1996 | Weerasooriya et al. | 562/123 |

FOREIGN PATENT DOCUMENTS

| | | |
|---|---|---|
| 0 225 143 | 6/1987 | European Pat. Off. . |
| 0241596 | 10/1987 | European Pat. Off. . |

OTHER PUBLICATIONS

Cracker/Derivative Unit Integration by David H. Purvis, Stone & Webster Engineering Corp. Tenth Ethylene Forum May, 1995.

Steamless Pyrolysis of Ethane to Ethylene, Chpt. 17, Y. Song L.J. Velenyi, A.A. Leff, WR Kliewer & J.E. Metcalfe, p. 319–339.

Westaim Surface Engineered Products, Website Information.

The Nickel–Complex Catalyzed Synthesis of α–Olefins by Arno Behr & Wilhelm Keim, The Arabian Journal for Science and Engineering, vol. 10, No. 4. pp. 377–390.

Primary Examiner—Walter D. Griffin
Attorney, Agent, or Firm—Kenneth H. Johnson

[57] ABSTRACT

A combined chain of a high temperature, high conversion steam cracker in combination with a polymerization or oligomerization unit provides capital and operating cost reduction.

39 Claims, 2 Drawing Sheets

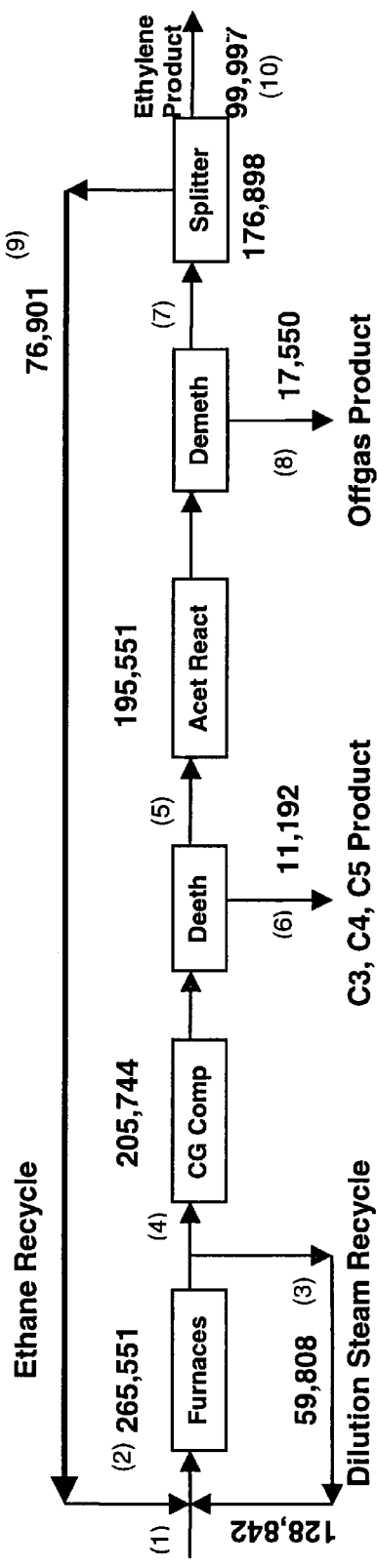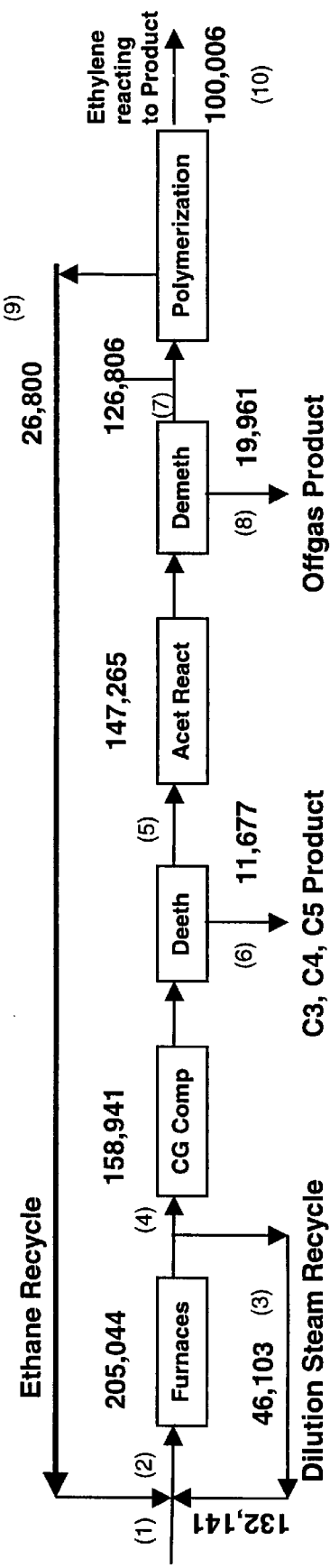
Figure 1a: Conventional Mass Balance [Tons/yr.]
Figure 1b: New Process Mass Balance [Tons/yr.]

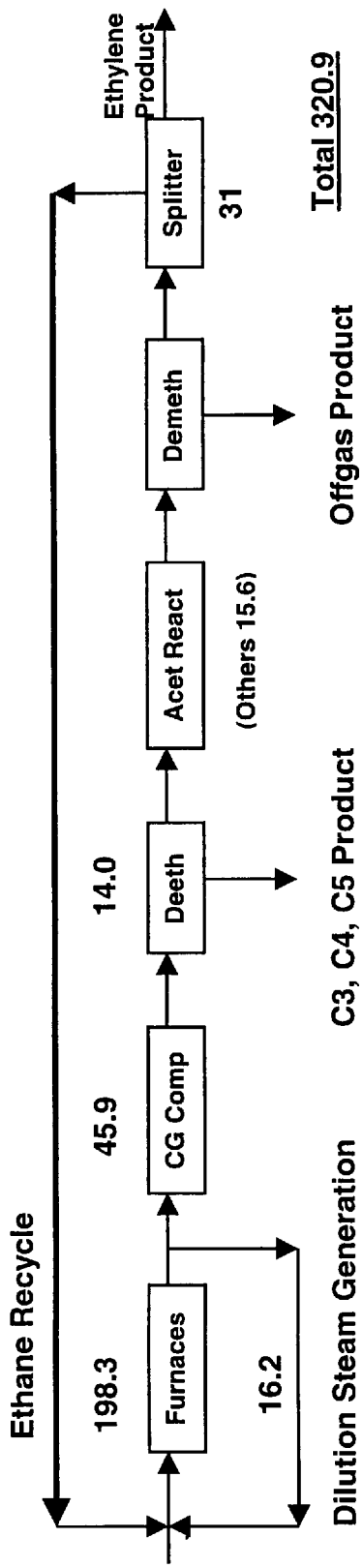
Figure 2a: Conventional Heat Balance [GJ/hr.]
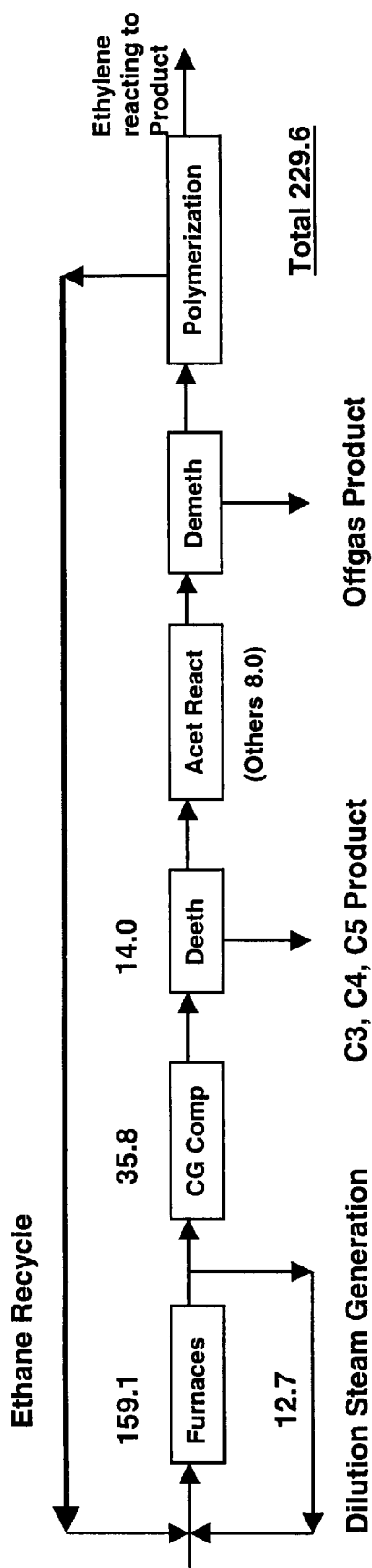
Figure 2b: New Process Heat Balance [GJ/hr.]

INTEGRATED HIGH TEMPERATURE HIGH CONVERSION OLEFIN/POLYOLEFIN PROCESS

FIELD OF THE INVENTION

The present invention relates to an integrated high temperature hydrocarbon cracking and olefin polymerization or oligomerization process. More particularly the present invention relates to an integrated process for preparing polyethylene and/or alpha-olefins from hydrocarbon feedstocks by high temperature cracking the hydrocarbon feedstocks, separating the $C_2$ fraction from the cracked gas into a feed comprising at least 75 weight % ethylene for polymerization or oligomerization. The advantages of this invention over the conventional method of cracking hydrocarbons, producing ethylene and polymerizing/oligomerizing the ethylene include: smaller load for the furnace, smaller cracked gas compressor, smaller acetylene processing unit, the absence of an ethane/ethylene splitter, a greatly reduced recycle of ethane, lower energy requirements, lower capital investment, lower operating costs and the possibility of packaging a small integrated ethylene/polyethylene or ethylene/alpha olefins plant.

BACKGROUND OF THE PRESENT INVENTION

At the Tenth Ethylene Forum, May 10–12, 1995, Stone and Webster presented a paper on the concept of an integrated ethylene plant and one or more down stream chemical plants to react dilute ethylene or propylene to produce a product such as polyethylene or polypropylene and the unreacted stream of dilute ethylene or propylene would then be recycled back to the ethane cracker. The benefit from the concept was twofold:

a reduction in the capital cost and operating cost of the ethylene unit.

a simple and cost effective way of debottlenecking existing ethylene units especially if already coupled to solution phase polyethylene units such as NOVA's SCLAIRTECH process. However, the paper failed to disclose high temperature ethylene furnaces or reactor materials to achieve high temperatures such as ceramic tubes or ceramic reactors.

In addition to the Stone and Webster paper, U.S. Pat. No. 5,430,211 issued Jul. 4, 1995 assigned to the Dow Chemical Company teaches the use of dilute ethylene produced using catalytic cracking to produce ethyl benzene. The patent is restricted to the use of catalytically dehydrogenated dilute ethylene.

U.S. Pat. No. 5,488,148 issued Jan. 30, 1996 assigned to the Vista Chemical Company claims the use of dilute ethylene in making sulfonated alkyl compounds.

Chapter 17, "Steamless Pyrolysis of Ethane to Ethylene" by Y. Sony, L. T. Velenyi, A. A. Leff, W. R. Kliewer and J. E. Metcalf (in the text Novel Production Methods for Ethylene, Light Hydrocarbons and Aromatics edited by L. F. Albright et al, Marcel Decker, Inc. N.Y. (1992)), teaches the high temperature cracking of ethane in ceramic furnace tubes, preferably silicon carbide at high temperatures.

None of the above art teaches an integrated high temperature cracking process to produce a 75 weight % ethylene feedstock integrated with a polymerization and/or oligomerization process or both together in parallel trains. Alpha olefins from oligomerization could be used directly as comonomers for polyethylene production.

SUMMARY OF THE INVENTION

The present invention provides an integrated process for the cracking of a feedstock to produce an ethylene rich stream and the subsequent polymerization or oligomerization of the ethylene stream without passing through an ethane/ethylene splitter comprising in cooperating arrangement the steps of:

i) feeding a feedstock to a cracker operated at a maximum allowable tube wall temperature of from 1050° C. to 1600° C.;

ii) passing the resulting product through a separation step to remove hydrocarbon streams having a carbon content of 3 and greater;

iii) subjecting the resulting stream to a treatment to convert acetylene to ethylene;

iv) removing the methane and hydrogen from the resulting stream to produce a product having an ethylene content from 75 weight % or more;

v) feeding the resulting stream to a polymerization or oligomerization process which has an inherent high ethylene conversion per pass (i.e. greater than 85%) and can operate effectively at feed ethylene concentrations as low as 75 weight %, and polymerizing or oligomerizing the ethylene; and vi) separating the unpolymerized stream from the polymer and solvent, and returning it to the ethylene unit.

DESCRIPTION OF THE DRAWING

FIG. 1a is a schematic flow diagram and mass balance of the conventional process for cracking a feed stock to produce ethylene and its subsequent polymerization.

FIG. 1b is a schematic flow diagram and mass balance of the process of the present invention for cracking a feed stock to produce ethylene and its subsequent polymerization.

FIG. 2a is a schematic flow diagram and heat balance of the conventional process for cracking a feed stock to produce ethylene and its subsequent polymerization.

FIG. 2b is a schematic flow diagram and heat balance of the process of the present invention for cracking a feed stock to produce ethylene and its subsequent polymerization.

DETAILED DESCRIPTION OF THE PRESENT INVENTION

As used herein the term maximum allowable tube wall temperature refers to the maximum temperature of the external surface of an ethylene furnace tube or coil exposed to the heating section of the cracker. Although we refer to tube or coil, other physical arrangements of the reaction chamber are possible.

The feedstocks for use in the present invention are well known to those of ordinary skill in the art. For example, feedstocks for use in accordance with the present invention include, but are not limited to, $C_{2-6}$ alkanes such as ethane, propane, butane, naphtha, raffinate, atmospheric gas oil, vacuum gas oil, distillate, crude oil, crude resids, and mixtures thereof, etc.

The present invention employs a high temperature cracking process which produces a cracked gas containing hydrogen, methane, $C_2$ hydrocarbons, $C_3$ hydrocarbons and heavier constituents.

The steam cracking process and other cracking processes are well known to those skilled in the art. Steam cracking processes are generally carried out in radiant furnace reactors at elevated temperatures for short residence times, at low reactant partial pressures, high gas velocity, and a low pressure drop through the reaction zone. Any of the furnace designs known to those skilled in the art may be employed in the practice of the present invention.

However, the coils or tubes should be adapted to have a high maximum allowable tube wall temperature. This refers to the outer surface of the tube or coil. Maximum allowable tube wall temperature may range from 1050° C. to 1400° C., depending on the material used and the operating severity (required conversion). For conventional HP alloys certain treatment helps to increase the tube life or reduce coking characteristics to permit a reasonable run length. For example, in the website "westaim.com" a tube or coil having an internal coating is described as Engineered Surface Coating by a company called WESTAIM. Typically, the metal beneath the coating comprises from about 23 to 35, preferably from 24 to 35 weight % of chromium. The metal may further comprise from 25 to 50, preferably from 30 to 45 weight % of nickel (Ni); from 1 to 3, preferably from 1.5 to 2.5 weight % of manganese (Mn); from 1 to 2, preferably from 1.5 to 2 weight % of silica (Si). The balance of the steel composition will be predominantly iron with other trace amounts (e.g. for elements other than carbon, typically less than 1 wt %, preferably from 0.1 to 1.0 weight %) of elements such as carbon, titanium, and tungsten, as is well known in the metallurgy arts.

The above tubes or coils may be used at maximum tube wall temperature from about 1050° C. to 1150° C. At these temperatures the conversion of the feedstock will result in about 75%–80% ethylene in the stream fed to the polymerization reaction in the absence of an ethane/ethylene splitter.

In a preferred embodiment of the invention, the tube or coil may be ceramic. These tubes may be used at maximum allowable tube wall temperatures of about 1200° C. to 1600° C.

The ceramic maybe silicon carbide in which case the maximum allowable tube wall temperature maybe from about 1200° C. to 1350° C. At these tube wall temperatures, a cracked gas stream is produced which contains ethylene in the mixed feed to the polymerization reactor which may range from about 80–97, preferred 90–97 weight %.

The hydrocarbon feed to the steam cracker is typically in vapor phase or it may comprise a mixed liquid-vapor phase. The most preferred feedstocks for steam cracking are $C_{2-4}$ alkanes, naphtha, and mixtures thereof.

Generally, preheated feed is introduced into a convection zone of a pyrolysis furnace to further preheat the feed to a temperature below that at which significant reaction takes place (e.g., 400° C. to 640° C.).

Typically small amounts of steam are added to the feed prior to introduction to the radiant reaction zone of the pyrolysis furnace to provide a weight ratio of from about 0.1 to 2 parts of steam to hydrocarbon, preferably from about 0.1 to 1 (based on the weight of the feed). The steam assists vaporization of the feed and reduces the hydrocarbon partial pressure in the reaction zone in order to improve olefin yields. The feed in process tubes or coils is then cracked at maximum tube wall temperature up to about 1400° C.

Typically operating conditions comprise an inlet temperature to the radiant heating section of the furnace ranging from about 600° C. to about 650° C. and an outlet temperature ranging from about 800° C. to about 1000° C.

The feed velocity through the coils ranges from about 300 to about 800 feet per second, based on the total flow of steam and hydrocarbons and also coil dimensions.

The residence time of the feed in the radiant section of the cracking coil generally ranges from about 30 to about 1000 milliseconds.

The effluent product gases issuing from the radiant zone are rapidly cooled to a temperature at which the cracking reactions substantially stop generally ranges from about 400° C. to about 600° C.

Generally, the effluent from the pyrolysis reactor is directed to a quench boiler wherein the effluent is indirectly contacted with cooling water in cooling tubes. After traversing the cooling tubes, the water is removed from the quench boiler in a line and returned to a supply tank.

The gaseous effluent from the cracking reaction then passes through an olefins purification system. Typically the gaseous effluent is water washed, compressed, caustic washed, compressed and then dried. The dried effluent is chilled and passes through a deethanizer to separate the effluent into two component streams; a light stream (e.g., hydrogen, methane, acetylene, ethane and ethylene), and a heavy stream (e.g., propane, propylene and mixed $C_4^+$ hydrocarbons). Then, the light product gases are compressed, and the acetylene components are removed by absorption or hydrogenated to ethylene in an acetylene hydrogenation reactor.

The effluent stream is cooled to a very low temperature typically from about −30° C. to about −60° C. and fed to a demethanizer to remove methane and hydrogen from the feed stream. The final treated effluent stream typically comprises from 70–99, preferably from 90–99 weight % of ethylene.

The effluent stream obtained from the olefins purification process may be employed as the feedstock for an ethylene polymerization or oligomerization process in accordance with the present invention. The feedstock for use in the polymerization process preferably contains at least about 75 weight % ethylene, more preferably at least about 85 weight % ethylene and most preferably from about 90 to 99 weight % ethylene.

The ethylene may be polymerized or oligomerized into polyethylene or alpha olefins either by solution, slurry or gas phase methods. Generally the pressure in the polymerization reactor for a solution process may exceed about 3,000 psi (e.g. about 3,000 to 10,000 psi, preferably from 3,000 to 5,000 psi). This moderate pressure is necessary to maintain the monomers and comonomers in solution even at the solution's high reaction temperature.

In these processes ethylene is dissolved in a liquid hydrocarbyl medium (e.g. $C_{5-10}$ alkyl and/or an aromatic hydrocarbon). The solution is contacted/mixed with a catalyst. The catalyst may be a conventional Ziegler Natta type catalyst, a metallocene type catalyst used by Exxon, a constrained geometry catalyst used by Dow or it could contain novel ligands such as phosphinimine ligands. Depending on the temperature the process may be a slurry process (polymer precipitates from solution) as are disclosed for example in patents to Phillips (typically below about 100° C.) or the polymer may remain in solution (temperature from 180° C. to 300° C.) as described in patents to, in the name of DuPont Canada, Novacor and Nova Chemicals Ltd.

The catalyst may also be Ni, Zr, Cr or Ti based oligomerization catalyst.

In the solution polymerization process the catalyst is deactivated and remains in the polymer. The polymer and solvent are then separated and the solvent is heated to remove residual unreacted feed (e.g., ethylene and ethane). The feed is then recycled to the cracker.

In the slurry polymerization process the polymer is separated from the diluent and the diluent is then heated to remove the unreacted feed. The polymerization may be a gas phase polymerization conducted at temperatures from about 80° C. to 115° C. at pressures from about atmospheric to 150 psig.

The current state of the art of gas phase polymerization process has low conversion per pass and inherently is not suitable for dilute ethylene utilization at this time. More advancements in catalyst technology and heat transfer might in future overcome this disadvantage.

In a further aspect of the present invention the ethylene from the cracker may be feed to an oligomerization unit. Typically these units condense ethylene into higher alpha olefins such as butene, hexene and octene although higher alpha olefins, up to about $C_{20}$, may be produced. Generally, in these processes, ethylene is contacted with a catalyst typically comprising of an aluminum alkyl (e.g. tri methyl aluminum or tri ethyl aluminum) or an aluminum complex of the formula $(R^4)_2AlO(R^4AlO)_mAl(R^4)_2$ wherein each $R^4$ is independently selected from the group consisting of $C_{1-20}$ hydrocarbyl radicals and m is from 0 to 50, preferably $R^4$ is a $C_{1-4}$ alkyl radical and m is from 5 to 30. The ethylene alpha olefin are at least recycled through a reaction or chain growth zone to grow the alpha olefin (e.g. increase the length by 2 carbon atoms (1 ethylene add on) as a result there is generally a statistical distribution of alpha olefins in the resulting product. The product is generally distilled to separate different alpha olefins. Generally, the process is conducted at pressures from about 2,000 to 5,000, preferably 2,000 to 3,500 psig and temperatures from about 90° C. to 180° C. Such processes are well known and described for example in U.S. Pat. No. 4,935,569 issued Jun. 19, 1990 assigned to Ethyl Corporation.

The ethylene stream from the cracker may also be fed to an oligomerization unit which uses transition metal complexes as catalysts and alkylaluminum compounds of the formula $AlR_xX_{3-x}$ as cocatalysts wherein R is a $C_{1-8}$, preferably $C_{1-4}$ alkyl radical, X is a halogen, preferably chlorine or bromine, and x is an integer from 1 to 3. Titanium, zirconium, hafnium, chromium, nickel or molybdenum could be used as active components of the complex catalysts. These processes require milder reaction conditions—pressures from 15 to 1500 psig and temperatures from 0° C. to 150° C. Such processes are known and described for example in "The Nickel-Complex Catalyzed Synthesis of α-Olefins" paper by Arno Behr and Wilhelm Keim in The Arabian Journal for Science and Engineering, Vol. 10, No. 4. or in the European Patent Application 241,596 published Nov. 21, 1987 the texts of which are herein incorporated by reference.

The present invention will be more fully described in association with the drawings. FIG. 1a and 1b are the simple mass balances generated by a computer program which accurately reflect commercial operations that compare the flow of materials. The calculations are based on a plant to produce 100,000 tons/yr. of ethylene going into a polyethylene unit. In the figure the bold numbers are tons of product.

Fresh feed stream (1) is introduced into the furnace in combination with dilution steam stream (3) and ethane recycle stream (9) respectively. The mass going through the furnace is therefore stream (2)=[(1)+(3)+(9)]. After cracking in the furnace and quenching, water is recovered and dilution stream is recycled.

The compressor which receives the cracked gases (stream 4) boosts the pressure of the stream before it goes to a deethanizer. From the deethanizer, $C_3$'s and heavier products are separated as stream (6) from the lighter fractions. The $C_2$'s and lighter materials (stream 5) enter the acetylene removal/conversion system and from there to the demethanizer. Off gases made up mainly of methane and hydrogen are removed as stream (8) while stream (7) in a conventional process goes to an ethane splitter. There ethane is separated from ethylene product (stream 10) while ethane from the stripper is recycled back to the furnace (stream 9). The figures illustrate the following improvements arising from the present invention as seen in Tables 1 to 3.

TABLE 1

Comparison Arising From Mass Balances

| Mass Flow | Invention (metric tons/yr) | Prior Art (metric tons/yr) |
| --- | --- | --- |
| To Cracking Furnace | 205,044 | 265,551 |
| Load on Compressor | 158,941 | 205,774 |
| C3 + Products | 11,677 | 11,192 |
| Acetylene Reactor | 147,265 | 195,551 |
| Offgas | 19,961 | 17,550 |
| Load to Splitter | 0 | 176,898 |
| Ethane Recycle | 26,800 | 76,901 |

In the process of the present invention illustrated in FIG. 1b, a polyolefins or oligomerization unit serves as the separator, and the unreacted ethane is recycled back to the furnace. The advantages of this over the conventional method become obvious to anyone knowledgeable in the art, when one studies Tables 1 to 4, as follows:

a smaller load for the furnace a smaller cracked gas compressor a smaller acetylene processing unit the absence of an ethane/ethylene splitter a greatly reduced recycle of ethane a small integrated ethylene/polyethylene unit reduced energy requirements lower operating costs The capital cost for the process of this invention compared to the conventional process, for the same plant capacity, is lower.

FIGS. 2a and 2b show the heat balances for both the conventional and the new process. The heat loads are given in gigajoules per hour. The total energy requirements for the conventional system is 320.9 GJ/hr as opposed to 229.6 GJ/hr for the new process. Tables 2 to 4 show the Energy Requirements, Energy Consumption/Generation and Operating Cost respectively for the prior art versus the invention.

TABLE 2

Energy Requirements

| | Invention [GJ/hr.] | Prior-Art [GJ/hr.] |
| --- | --- | --- |
| Furnace | 159.1 | 198.3 |
| Cracked Gas Compressor Driver | 35.8 | 45.9 |
| Dilution Steam Generation | 25.3 | 16.2 |
| Deethanizer Chilling train | 14.0 | 14.0 |
| C2 Splitter (C3 Refrigeration) | 0.0 | 31.0 |
| Auxiliary Firing (Steam) | 21.9 | 15.6 |
| TOTAL | 256.1 | 320.9 |

TABLE 3

Energy Consumption/Generation

| | Invention [GJ/metric ton of Ethylene] | Prior-Art [GJ/metric ton of Ethylene] |
|---|---|---|
| Energy Consumption | 15.21 | 17.95 |
| Energy Generation (Off-gases only) | 14.85 | 13.52 |
| Carbon Dioxide (off-gases only) | 0.295 | 0.237 |

TABLE 4

Operating Costs

| | Invention [$/Megagram] | Prior-Art [$/Megagram] |
|---|---|---|
| Ethane | 232.1 | 226.3 |
| Offgas | (40.7) | (37.4) |
| C3s | (9.4) | (14.3) |
| C4s | (18.4) | (13.6) |
| C5s | (9.5) | (8.9) |
| Energy | 39.5 | 46.6 |
| TOTAL | 193.5 | 198.7 |

The conditions for the simulation are as follows:

Inlet pressure: around 1.97 kg/cm$^2$ A

Internal Diameter: 0.038 M

Coil Residence Time 120 ms

Dilution Steam Ratio (kg steam/kg ethane)=0.3

The conventional runs were simulated for 65% ethane conversion in the furnace, while the new process runs were simulated for 88% ethane conversion.

EXAMPLE 1

Table 5 shows the effect of Coil Outlet Temperature on ethylene yield based on computer simulations of an ethylene cracker.

TABLE 5

The Effect of Coil Outlet Temperature on Ethylene Yield

| Coil Outlet Temperature (COT) [° C.] | Ethylene Yield [wt. %] |
|---|---|
| 875 | 47.97 |
| 889 | 52.63 |
| 901 | 55.83 |
| 910 | 58.15 |
| 919 | 60.14 |
| 929 | 61.78 |
| 932 | 62.30 |
| 938 | 63.09 |
| 946 | 64.10 |
| 950 | 64.39 |
| 958 | 65.01 |
| 967 | 65.36 |

EXAMPLE 2

Once through yields of ethylene for high conversion process which enables the close coupling with a polymerization or oligomerization unit were calculated at various conversions (temperatures) using computer programs which closely simulate actual plant operation. The results are shown in Table 6.

TABLE 6

Yields (WT %) of Components AT

| Components | 65% Ethane Conversion | 85% Ethane Conversion | 90% Ethane Conversion | 95% Ethane Conversion |
|---|---|---|---|---|
| Methane | 2.9 | 7.0 | 7.6 | 7.6 |
| Acetylene | 0.7 | 2.7 | 3.9 | 4.6 |
| Ethylene | 52.6 | 65.0 | 65.4 | 66.3 |
| Ethane | 36.4 | 12.2 | 10.2 | 5.9 |
| C$_3$'s & heavier | 3.4 | 7.4 | 7.9 | 8.8 |

The rest are off-gases (CO, CO$_2$, H$_2$)

EXAMPLE 3

Table 7 shows the effect of conversion on Maximum Allowable Tube Metal Temperature (MATMT) for runs of various duration's of time. In the table the subscript is the run length in days and 0 is start up. The table shows that the material of construction must be carefully chosen to be able to attain the required conversion with economically adequate run length.

TABLE 7

The Effect of Conversion on Maximum Allowable Tube Metal Temperature (MATMT)

| Ethane Conversion [%] | (MATMT)$_0$ [° C.] | (MATMT)$_{10}$ [° C.] | (MATMT)$_{20}$ [° C.] | (MATMT)$_{30}$ [° C.] |
|---|---|---|---|---|
| 56.03 | 986 | 1006 | 1017 | 1031 |
| 63.64 | 990 | 1037 | 1052 | 1071 |
| 68.54 | 1007 | 1060 | 1079 | 1103 |
| 72.35 | 1020 | 1080 | 1102 | 1129 |
| 75.87 | 1033 | 1098 | 1125 | 1155 |
| 79.09 | 1045 | 1116 | 1146 | 1180 |
| 80.19 | 1050 | 1123 | 1154 | 1189 |
| 82.00 | 1057 | 1133 | 1167 | 1204 |
| 84.62 | 1068 | 1150 | 1187 | 1227 |
| 85.51 | 1072 | 1156 | 1194 | 1235 |
| 87.77 | 1082 | 1171 | 1213 | 1256 |
| 89.79 | 1092 | 1186 | 1231 | 1277 |

What is claimed is:

1. An integrated process for the cracking of a feedstock selected from the group consisting of C$_{2-6}$ alkanes, naphtha, raffinate, atmospheric gas oil, vacuum gas oil, distillate, crude oil, crude resids, and mixtures thereof to produce ethylene and the subsequent polymerization or oligomerization of the ethylene, in the ethane/ethylene stream, without passing through an ethane splitter comprising in cooperating arrangement the steps of:

i) feeding the feedstock to a steam cracker comprising furnace tubes passing through a radiant furnace reactor operated at a maximum allowable furnace tube wall temperature of from 1050° C. to 1600° C. and a quench section operated at temperatures from 400° C. to 600° C. comprising tubes passing through a cooling medium to yield a cracked gas comprising hydrogen, methane, C$_2$ hydrocarbons, C$_3$ hydrocarbons and heavier constituents;

ii) passing the cracked gas from step i) through a separation step to remove hydrocarbon streams having a carbon content of 3 and greater leaving a stream of hydrogen, methane, acetylene, ethane and ethylene;

iii) subjecting said stream of hydrogen, methane, acetylene, ethane and ethylene to a treatment to convert acetylene to ethylene;

iv) removing the methane and hydrogen from the resulting stream from step iii) of hydrogen, methane, ethane and ethylene to produce a product having an ethylene content from 75 weight % to 95 weight %;

v) feeding the resulting stream from step iv) of ethane and ethylene having an ethylene content from 75 weight % to 95 weight % to a polymerization or oligomerization process and polymerizing or oligomerizing the ethylene; and vi) recovering the unreacted ethylene and ethane and returning them to the steam cracker.

2. The process according to claim 1, wherein the feed from step iv) is fed to a polymerization process.

3. The process according to claim 2, wherein the polymerization is a solution, slurry, or gas phase operated process.

4. The process according to claim 3, wherein the feedstock is selected from the group consisting of ethane, naphtha and gas oil.

5. The process according to claim 4, wherein the residence time in the cracker is from 30 to 1000 milliseconds.

6. The process according to claim 5, wherein the furnace tubes in the cracker are austenitic stainless steel and the maximum allowable tube wall temperature is from 1050° C. to 1250° C.

7. The process according to claim 6, wherein the ethylene content in the feed to the polymerization reactor is from 75 to 85 weight %.

8. The process according to claim 7, wherein the polymerization process is a solution polymerization process operated at a pressure from 3,000 psi to 5,000 psi.

9. The process according to claim 8, wherein the conversion of ethylene to polyethylene is greater than 85%.

10. The process according to claim 7, wherein the polymerization process is a slurry polymerization process.

11. The process according to claim 10, wherein the conversion of ethylene to polyethylene is greater than 85% on a once through basis.

12. The process according to claim 7, wherein the polymerization process is a gas phase process.

13. The process according to claim 12, wherein the conversion of ethylene to polyethylene is greater than 85% on a once through basis.

14. The process according to claim 5, wherein the furnace reactor is ceramic or high temperature alloy and the maximum allowable tube wall temperature is from 1200° C. to 1600° C.

15. The process according to claim 14, wherein the ceramic is silicon carbide and the maximum allowable tube wall temperature is from 1200° C. to 1400° C.

16. The process according to claim 15, wherein the polymerization process is a solution polymerization process operated at a pressure from 3,000 psi to 5,000 psi.

17. The process according to claim 16, wherein the conversion of ethylene to polyethylene is greater than 85%.

18. The process according to claim 15, wherein the polymerization process is a slurry polymerization process.

19. The process according to claim 18, wherein the conversion of ethylene to polyethylene is greater than 85% on a once through basis.

20. The process according to claim 15, wherein the polymerization process is a gas phase process.

21. The process according to claim 20, wherein the conversion of ethylene to polyethylene is greater than 85% on a once through basis.

22. The process according to claim 1, wherein the feed from step iv) is fed to an oligomerization unit.

23. The process according to claim 22, wherein the feedstock is selected from the group consisting of ethane, naphtha and gas oil.

24. The process according to claim 23, wherein the residence time in the cracker is from 30 to 1000 milliseconds.

25. The process according to claim 24, wherein the furnace tubes in the cracker are austenitic stainless steel and the maximum allowable tube wall temperature is from 1050° C. to 1250° C.

26. The process according to claim 25, wherein the catalyst in the oligomerization unit is selected from the group consisting essentially of an alkylaluminum compound or a transition metal complex of titanium, zirconium, hafnium, chromium, nickel or molybdenum with or without an alkylaluminum compound.

27. The process according to claim 26, wherein the aluminum compound is selected from the group consisting of the tri ethyl aluminum and tri methyl aluminum.

28. The process according to claim 26, wherein the aluminum compound has the formula $AlR_xX_{3-x}$ wherein R is a linear or branched alkyl radical comprising 2 to 8 carbon atoms, X is chlorine or bromine and x is equal to 1, 2 or 3.

29. The process according to claim 26, wherein the aluminum compound has the formula $(R^4)_2AlO(R^4AlO)_mAl(R^4)_2$ wherein each $R^4$ is independently selected from the group consisting of $C_{1-4}$ alkyl radicals and m is from 5 to 30.

30. The process according to claim 24, wherein the furnace reactor is ceramic or high temperature alloy and the maximum allowable tube wall temperature is from 1200° C. to 1600° C.

31. The process according to claim 30, wherein the ceramic is silicon carbide and the maximum allowable tube wall temperature is from 1200° C. to 1400° C.

32. The process according to claim 31, wherein the catalyst in the oligomerization unit is selected from the group consisting essentially of an alkylaluminum compound or a transition metal complex of titanium, zirconium, hafnium, chromium, nickel or molybdenum with or without an alkylaluminum compound.

33. The process according to claim 32, wherein the aluminum compound is selected from the group consisting of the ethyl aluminum and tri methyl aluminum.

34. The process according to claim 32, wherein the aluminum compound has the formula $AlR_xX_{3-x}$ wherein R is a linear or branched alkyl radical comprising 2 to 8 carbon atoms, X is chlorine or bromine and x is equal to 1, 2 or 3.

35. The process according to claim 32, wherein the aluminum compound has the formula $(R^4)_2AlO(R^4AlO)_mAl(R^4)_2$ wherein each $R^4$ is independently selected from the group consisting of $C_{1-4}$ alkyl radicals and m is from 5 to 30.

36. The process according to claim 30, wherein the catalyst in the oligomerization unit is selected from the group consisting essentially of an alkylaluminum compound or a transition metal complex of titanium, zirconium, hafnium, chromium, nickel or molybdenum with or without an alkylaluminum compound.

37. The process according to claim 36, wherein the aluminum compound is selected from the group consisting of the tri ethyl aluminum and tri methyl aluminum.

38. The process according to claim 36, wherein the aluminum compound has the formula $AlR_xX_{3-x}$ wherein R is a linear or branched alkyl radical comprising 2 to 8 carbon atoms, X is chlorine or bromine and x is equal to 1, 2 or 3.

39. The process according to claim 36, wherein the aluminum compound has the formula $(R^4)_2AlO(R^4AlO)_mAl(R^4)_2$ wherein each $R^4$ is independently selected from the group consisting of $C_{1-4}$ alkyl radicals and m is from 5 to 30.

* * * * *